United States Patent [19]
Munce

[11] Patent Number: 5,658,149
[45] Date of Patent: Aug. 19, 1997

[54] DEDICATED CHANNEL FOR ROOT CANAL ACCESS

[76] Inventor: C. John Munce, 1525 State St., Ste. 201, Santa Barbara, Calif. 93101

[21] Appl. No.: 525,389

[22] Filed: Sep. 8, 1995

Related U.S. Application Data

[63] Continuation of Ser. No. 257,959, Jun. 10, 1994, abandoned, which is a continuation-in-part of Ser. No. 69,026, May 26, 1993, abandoned.

[51] Int. Cl.$^6$ ........................................... A61C 5/02
[52] U.S. Cl. .............................. 433/224; 433/102
[58] Field of Search ........................... 433/81, 102, 224, 433/75, 76

[56] References Cited

U.S. PATENT DOCUMENTS

| | | | |
|---|---|---|---|
| 1,711,952 | 5/1929 | Kulik | 433/224 |
| 3,330,040 | 7/1967 | Kahn | 433/224 |
| 3,534,476 | 10/1970 | Winters | 433/224 |
| 4,608,017 | 8/1986 | Sadohara | 433/81 |

FOREIGN PATENT DOCUMENTS

| | | | |
|---|---|---|---|
| 0205937 | 12/1986 | European Pat. Off. | 433/102 |
| 2034174 | 1/1972 | Germany | 433/102 |
| 3734303 | 4/1989 | Germany | 433/224 |

*Primary Examiner*—Cary E. O'Connor
*Attorney, Agent, or Firm*—Michael G. Petit

[57] ABSTRACT

A device is described which is useful for providing a dedicated access channel to the root canal of a tooth. The device, which is the frustum of a cone, has a hollow interior passageway adapted to receive and loosely accommodate the shank of a standard assortment of endodontic files. The vertical length of the cone is approximately 10 mm to 15 mm. The wider end of the conical device has an outer diameter of approximately 2.5 millimeters. In practice, the orifice of a root canal is exposed by drilling an access cavity. An appropriately sized endodontic file is selected which will fit within the orifice of the canal. The conical device is slid over the endodontic file until the wider end of the cone is adjacent to the file handle. The file tip is then inserted into the root canal, and the conical device is slid down the shaft of the file until it is brought to bear against the floor of the access cavity with the narrow end of the conical device juxtaposed to the exposed orifice of the root canal. A projected canal matrix material is carefully injected around the endodontic file and the entire access cavity is filled with a suitable self-curing matrix material, such as glass ionomer, to the biting surface. After the matrix solidifies, the file and conical device are removed leaving a conical access channel to the canal orifice.

7 Claims, 4 Drawing Sheets

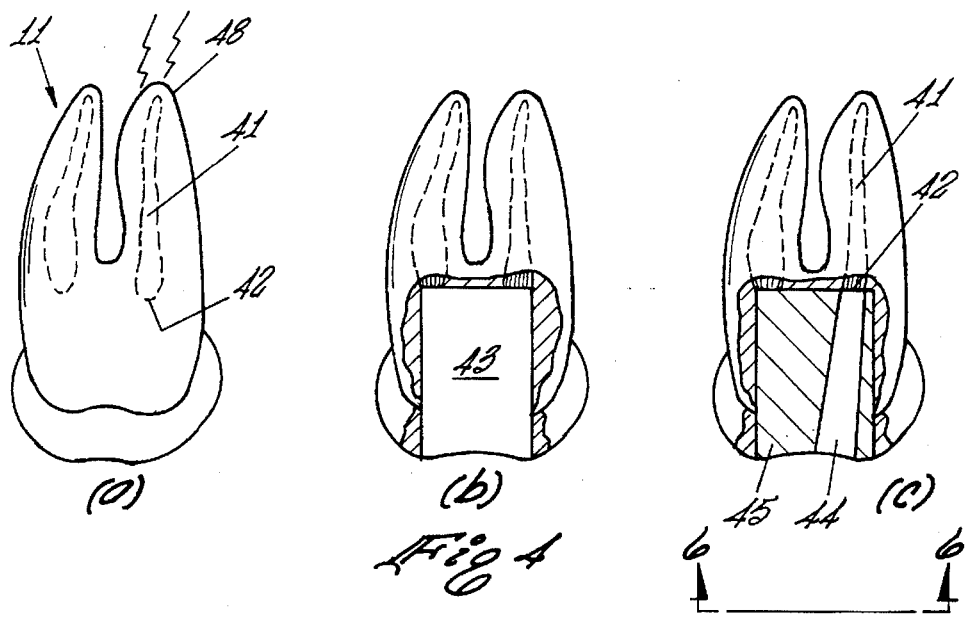
Fig. 4
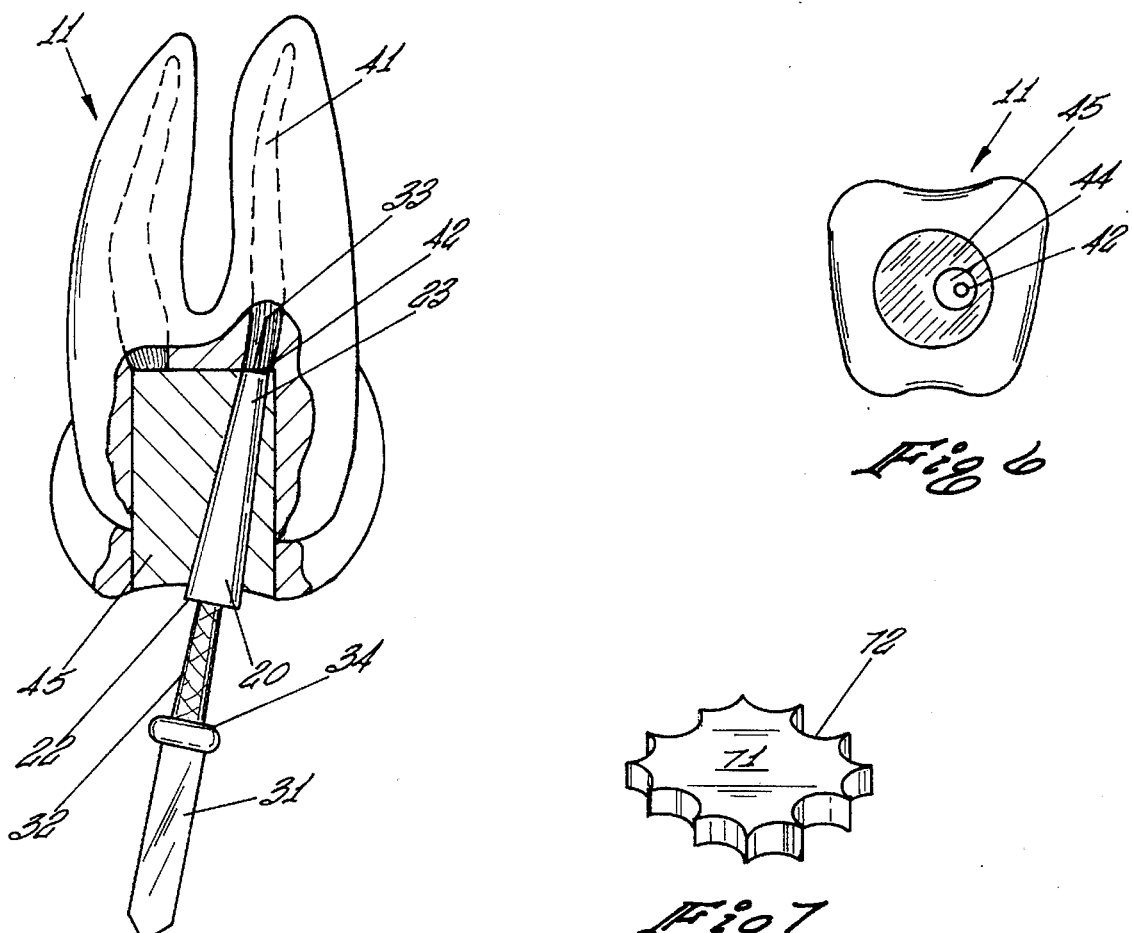
Fig. 5
Fig. 6
Fig. 7

5,658,149

DEDICATED CHANNEL FOR ROOT CANAL ACCESS

CROSS REFERENCE TO RELATED APPLICATIONS

This is a continuation of application Ser. No. 08/257,959; filed Jun. 10, 1994, now abandoned, which is a continuation-in-part of application Ser. No. 08/069,026, filed May 26, 1993, now abandoned.

BACKGROUND OF THE INVENTION

1. Field of the Invention

This invention relates to a device and method for performing root canal procedures in dentistry.

2. Prior Art

Root canal procedures are well known in the art. When the pulp of a tooth becomes infected, an abscess may form. The tooth must be treated by cleaning out the dead or infected pulp from the root canal, destroying any bacteria and then filling and sealing the canal and restoring the crown. It is customary to expose the root canal orifice by drilling away a portion of the clinical crown of the tooth to an appropriate depth. Once the orifice of the root canal is exposed, an endodontic file or similar instrument may be inserted into the root canal to remove the tissue. Endodontic files are extremely small and easily kinked or otherwise bent if the file tip encounters hard tooth structure on the walls or floor of the access cavity rather than entering directly into the intended canal orifice. Additionally, prior art procedures normally require the insertion of the file through the access cavity created in the clinical crown of the tooth using a mirror or similar device to view the canal orifice, as the orifice is generally not accessible to direct vision.

It is, therefore, desirable to provide a projected or dedicated access channel for endodontic instruments whereby such instruments are easily introduced into the root canal without the need for a mirror. Further, after insertion of a root canal instrument into such an improved access channel, the root canal instrument(s) should be able to be manipulated conveniently throughout the length of the root canal.

SUMMARY OF THE INVENTION

To facilitate placement of an endodontic file into the root canal orifice the canal may be "projected." Such a "projection" of the root canal to form a dedicated access channel may be accomplished by exposing the canal orifice via excavation with a drill to form an access cavity and placement of an endodontic file tip into the canal orifice. The region around the endodontic file may then be filled with a self-curing plastic material such as composite, glass ionomer, or various dental cements. After the plastic material has hardened, the file may then be removed leaving behind a channel through which the file may be repeatedly re-inserted to access the root canal. A problem with such a dedicated channel is that the diameter of the channel is necessarily the same as that of the file used to create it. Thus, since the file is tapered, it is not possible to insert the tip of the file all the way to the terminus of the root canal because of the constriction of the walls of the channel. Further, the small size of the projected or dedicated channel makes it difficult to place the endodontic file in the projected channel opening in the cavo-surface of the tooth. Consequently, considerable manipulation of the instruments within the created channel is required in order to enlarge it.

It is an object of this invention to provide an access channel to the root canal of a tooth which is projected to facilitate introduction of an endodontic instrument into the root canal.

It is another object of this invention to provide an access channel which is substantially conical in shape.

It is another object of this invention to provide a projected channel for gaining access to the root canal of a tooth which channel effectively "stiffens" or supports an endodontic file to prevent kinking of the file.

It is another object of this invention to provide a device and method for using the device which will facilitate the repair of pulp chamber perforations and root perforations while maintaining an access channel to the root canal.

It is another object of this invention to facilitate pre-treatment coronal build-ups of badly broken-down teeth while maintaining an access channel to the root canal.

It is another object of this invention to provide a device and a method for using the device which can facilitate the controlled hydraulic dissemination of root canal sealer throughout the prepared root canal space.

These and other objects of the invention will soon become apparent as we turn now to the description of the preferred embodiments.

BRIEF DESCRIPTION OF THE DRAWINGS

FIG. 4a is a partially cross-sectional view of the tooth indicated in FIG. 1 with two of the root canals identified as a phantom.

FIG. 4b is a partially cut-away view of the tooth of FIG. 4a which has been excavated to expose a root canal orifice.

FIG. 4c shows the tooth of FIG. 4b after the conical device has been employed to create a dedicated root canal access passage in the matrix material injected around it.

FIG. 5 is an enlarged view of the tooth of FIG. 4c showing the endodontic file and the conical device of the present invention in position during polymerization of the plastic matrix material.

FIG. 6 is an end-on view of the tooth of FIGS. 4a–c showing the cavo-surface of the dedicated root canal access channel after the file and conical device have been removed.

FIG. 7 is a perspective view of a file separator useful for positioning one or more conical devices with respect to one another.

DESCRIPTION OF THE PREFERRED EMBODIMENTS

Figure 1:
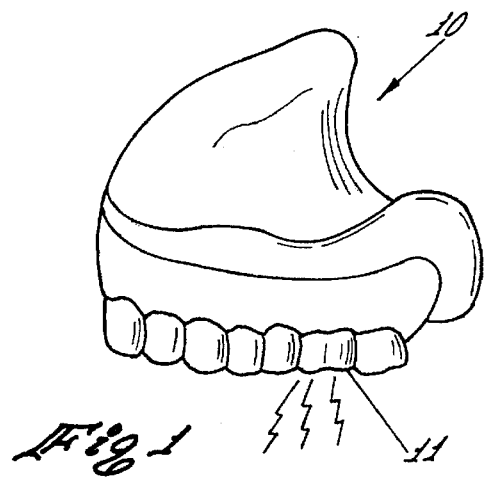
FIG. 1 is a perspective view of the upper jaw showing a tooth in need of root canal treatment.

Turning now to FIG. 1, an upper jaw is shown generally indicated at 10, with a tooth 11 which requires a root canal procedure. The tooth 11 may be located towards the back of the mouth as shown making it relatively difficult to view the deep structures of the tooth during the procedure.

Figure 2:
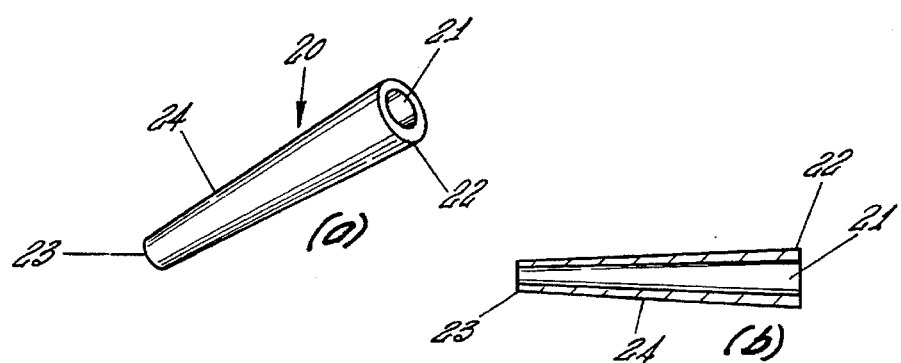
FIG. 2a is a perspective elevational view of the conical device of the present invention.
FIG. 2b is a horizontal cross-sectional view of the conical device of the present invention.
Figure 3:
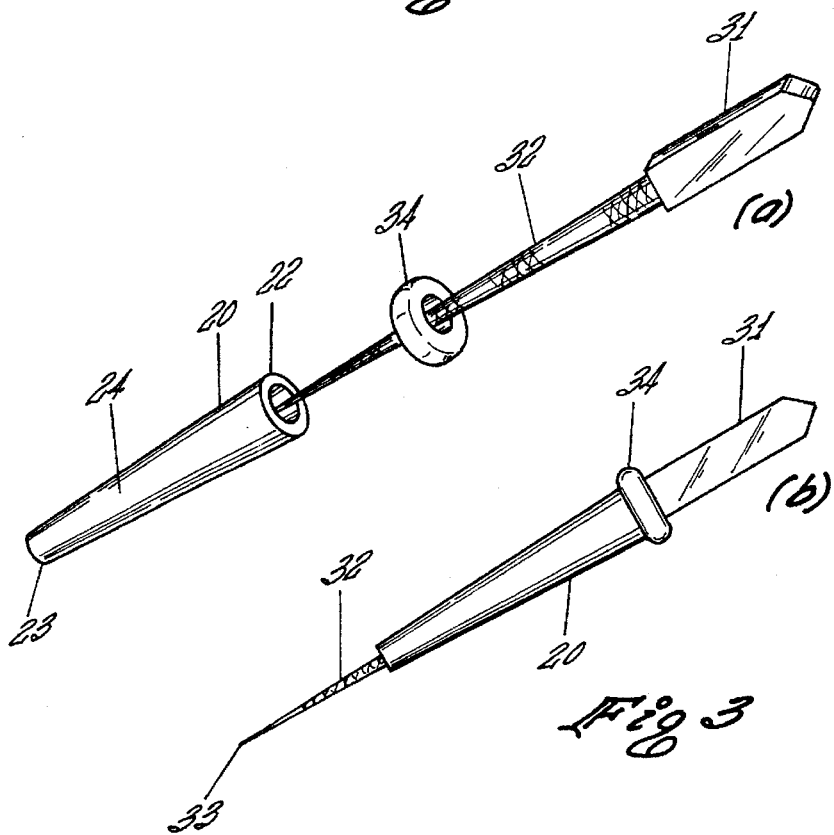
FIG. 3a is a somewhat schematic elevational perspective view of the conical device of the present invention in relationship to an endodontic file prior to use.
FIG. 3b is the same as FIG. 3a with the conical device of the present invention positioned against the rubber stopper of the endodontic file prior to use.

A preferred embodiment of the conical device of the present invention is shown in FIGS. 2 and 3. The conical device 20, shown in perspective in FIG. 2a and horizontal cross-section in FIG. 2b, serves as a template for the root canal access channel. The device 20 is the frustum of a cone with a central longitudinal conduit 21 coextensive therewith dimensioned to accommodate the shank of an endodontic file 32 ranging in size from approximately size 06 to size 50. The vertical length of the conical device 20 is approximately 10 to 15 millimeters; the wider end 22 having an outer diameter of about 2.5 mm which is approximately the diameter of the handle 31 of an endodontic file 32. The outer wall 24 of the conical device 20 is continuously tapered from the wider end 22 to the narrow end 23 at which narrow end 23 the file 32 emerges from the conical device approximately 10 to 15 millimeters from the wider end 22. In order to accommodate all diameters of endodontic files, the conical device 20 should have a slightly oversized central conduit 21, and the flat surface of the wider end 22 is preferably coated with a contact type of adhesive such that when the wider end 22 is brought into contact with the endodontic rubber stop 34 on the shank of the endodontic file 32, the wider end 22 releasably adheres to the stop 34 so that the entire rubber stopper-conical device complex can be moved at will up and down the shaft of the endodontic file 32 no matter what the size of the file. Furthermore, to accommodate larger-diameter endodontic files, the narrow tip 23 of the plastic cone 20 may be snipped off with a pair of clinical scissors prior to use.

FIG. 4a is an exploded view of the tooth 11 identifying a root canal phantom 41 which contains tissue that must be removed. The root canal 41 generally extends to somewhere near the apex 48 of the root on one end and into the clinical crown 42 at the other end. In FIG. 4b, an access cavity or chamber is created by excavating a portion of the tooth 43 to expose the canal orifice 42 providing access to the root canal 41.

In practice, the device 20 of the present invention is placed over the shank or shaft of an endodontic file 32 and slid up the shaft to a rubber stopper 34 as shown in FIG. 3b. The shaft tip 33 of the endodontic file is then placed into the orifice 42 of the root canal 41 and the conical device 20 is slid down the shaft of the file until the narrow tip 23 of the conical device 20 is brought to bear against the peri-orifice dentin in the access chamber floor as shown in shown in FIG. 5. A suitable self-curing matrix material 45 such as glass ionomer is then injected around the conical device 20 to fill the excavation. The matrix material 45 is allowed to polymerize. The file 32 is then removed taking with it the conical device 20 and leaving behind a funnel-shaped access channel 44 (FIG. 4C) which provides facile access to the root canal 41. The surface of the tooth 11 showing the access channel 44 and surrounding polymerized matrix material 45 is shown in FIG. 6.

Use of the conical device 20 mitigates difficulties which arise as a result of embedding very small endodontic instruments such as a No. 06, 08 or 10 file, within the self-curing "projected canal" matrix. Except when one is attempting to bypass an obstruction within a root canal system, or attempting to auger small instruments past calcifications within the canal, the conical device of the present invention can be used to advantage to create a conical access channel to the root canal orifice. When file "stiffening" is required, it is advantageous for the matrix of the dedicated channel to remain very tight around the small endodontic instrument to provide the torsional support required to prevent kinking of the file. Even in these cases, the device may be useful, provided it is not pushed all the way to the level of the chamber floor. I.e., in such cases, the device is only introduced by 3–5 mm into the self-curing matrix. However, in the majority of cases of projected canals, a significant advantage may be gained by creating a conical shape from the cavo-surface to the actual canal orifice in the floor of the chamber. This significantly reduces the work required and therefore the time necessary to enlarge the body of the canal by eliminating the need to enlarge the channel created within the matrix.

The conical device may be fabricated using a variety of materials. Plastic injection molded conical devices are easily released by glass ionomer and are relatively inexpensive, rendering them disposable. The conical device may also be fabricated using a more durable material such as surgical stainless steel which may be reused. Whatever the choice of material, the surface of the conical device should either readily release the matrix material or be coated so that it will readily release the polymerized matrix material.

EXAMPLE OF THE PROCEDURE

After endodontic access cavity preparation with a dental drill, an appropriately sized endodontic file is selected to fit well within the orifice of the canal. The conical device described above is slipped onto the endodontic file, wide end toward the file handle, and adhered to the rubber stopper. The conical device/stopper complex is elevated such that the rubber stopper is touching the endodontic file handle. The file tip is inserted well within the canal orifice and the conical device is slid down the shaft of the file until it is brought to bear against the floor of the excavated chamber at the orifice of the root canal. The projected canal matrix material is carefully injected around the orifice and the device. The entire chamber is filled with self-curing matrix to the cavo-surface. Upon polymerization of the matrix, the file is removed. If the conical device is not released upon withdrawal of the file, it may be removed by the use of a large Hedström file inserted tightly within the channel of the conical device, rotating the file to engage the flutes into the conical device and withdrawing.

In the case of multiple canals, files prepared as described are inserted into each canal orifice prior to injection of the projection matrix. Often it is advantageous to pre-bend the files so as to create emergence profiles such that there is no intersection of the files within the access cavity. It may also be desirable to use different sized files (represented by different colored handles) so as to facilitate identification of the canal represented by a particular emerging file. Files often require physical separation from each other while the matrix remains plastic. Forcing an emerging file in an inappropriate direction could lead to significant instrumentation difficulties later in the procedure. Upon polymerization of the matrix, the files and conical devices are removed as previously described.

The device may also be used to facilitate effective non-surgical repair of perforations of the floor of the pulp chamber or of the tooth root itself. Perforations may be either pathogenic such as in the case of resorptive perforations or iatrogenic such as in the case of clinical mishaps. In many such cases, the tooth cannot be saved. In other cases, the tooth may be saved provided a surgical repair is performed. However, using the described invention, such teeth may often be saved without the need for surgical procedures.

After identification of the perforation, an appropriate material (freeze-dried bone, tri-calcium sulfate, tri-calcium phosphate, or some combination of these or other materials well-known in the art) is condensed through the perforation site into the adjacent bone to control bleeding and to provide a matrix against which repair material may be placed. If the defect is in or near the pulp chamber floor, files fitted with the conical device are then placed within all canals, the devices are slid down the shaft of the files to the level of the access chamber floor, and the projection/repair matrix is injected to the cavo-surface as previously described. Following polymerization, files and conical devices are removed, and instrumentation and obturation proceed as usual. However, if the defect is a perforation deeper within the root, insertion of a file must be "practiced" prior to injection of the projection/repair matrix such that the file can be consistently delivered to the canal without entering the perforation. Once this is mastered, the projection/repair matrix is passively injected directly into the body of the canal itself ensuring that it reaches the perforation site in sufficient bulk to effect an adequate repair. Thereafter, the file, fitted with the conical device described, is re-inserted into the body of the canal as "practiced," the conical device is slid to the level of the chamber floor, and the chamber is filled to the cavo-surface with the projection/repair matrix. The caveat to instrumentation of the canal with a perforation repair in the body of the root is that aggressive instrumentation may weaken the repair such that the perforation may be re-opened during instrumentation or may herniate during obturation. In such cases, "light" instrumentation is required.

The conical device may also be used for file "stiffening" when very tiny root canal files are employed to negotiate past obstructions in the root canal system. An obstruction may be biologic, such as a calcified canal, or it may be iatrogenic, such as a broken instrument or other foreign object occluding the canal.

Small instruments frequently may be advanced until the tip is adjacent to the blockage but because the instruments are so delicate they cannot be further advanced. When pressure is applied, the instruments kink, and must be discarded and another obtained. This is expensive, time consuming, and frequently leads to treatment failure. If a very small instrument fitted with the described invention is advanced until the tip of the instrument "sticks" alongside of the obstruction, a self-curing material may be injected around it. In certain cases, it may be advantageous to inject the material first and thereafter-to insert the file to the point at which it "sticks". This sequencing, however, requires insertion "practice" as previously described. As mentioned earlier, glass ionomer is particularly useful for this purpose. While the projection matrix remains plastic, the conical device is slid down the shaft of the file until the tip of the device penetrates the matrix by 3 to 5 mm. After the material polymerizes, the instrument and the conical device may be withdrawn leaving an easily visualized and readily accessible "dedicated channel" through which one can reinsert a very small diameter instrument without the use of a dental mirror for visualization. The tip of the reinserted instrument returns exactly to it's initial position. Further, the instrument is completely surrounded by material and cannot bend. This is referred to hereinafter as "file stiffening". File stiffening imparts a tremendous stiffness to the instrument that it otherwise does not possess. It allows one to take an 0.06 mm or 0.08 mm endodontic file, which is very delicate, insert it and auger it past an obstruction.

Glass ionomer is a nearly ideal self-curing matrix forming material. A problem with glass ionomer, however, is that it is tooth colored. If, after the procedure, it is desirable to completely remove standard glass ionomer, it may be difficult to distinguish matrix from tooth. A glass ionomer of contrasting color would be desirable for this purpose.

Glass ionomer is a self-curing, fluoride-emitting material that has been used in dentistry for many years. It has the unique ability to bond to dentin. Glass ionomer may be left in place if it is to be covered with a crown, and if it is not required to withstand a great deal of stress. However, in those cases where there is little tooth structure remaining, immediately following the root canal procedure, the glass ionomer should be removed and replaced with a more reliable restorative material.

When sealer is hydraulically disseminated throughout the root canal system, a small amount may escape into the surrounding tissues through various portals of exit. Thus it is important to control the pressure which determines how much sealer actually escapes through these exits. Some sealers are radio-opaque. Radiographically, it is desirable to see a small sealer puff at the portals of exit. It is undesirable to have a large volume of sealer expressed through the exits of the root canal system. If an endodontic plugger is used to apply pressure, excess pressure may force too much sealer through the portals of exit. To enhance the hydraulic dissemination of sealer throughout the irregularly-shaped space of the prepared root canal, the described conical device may be used. After the root canal space is completely cleaned, shaped, and passively filled with sealer, the conical device is repositioned in the cone-shaped dedicated channel that has been created in the coronal structure of the tooth. A relatively large gauge endodontic file (a #50, #55 or #60 Hedström) is then inserted through the hole of the conical device. Rotating the file 5 or 6 times brings a precise amount of hydraulic pressure to bear on the space inside the root canal causing the sealer to be expressed throughout the root canal system in a controlled manner. This controllable pressure on the sealer fills the lateral canals, loops, fins and other irregularities of the root canal space.

The conical device may then be removed by simply withdrawing the Hedström file. Gutta percha is then inserted through the funnel-shaped passageway directly into the root canal space, and the root canal is obturated. After insertion, gutta percha may be thermoplasticized such that it becomes amorphous and joins with the sealer.

A kit (shown at 80 in Figures) is particularly useful for creating dedicated root canal access channels. The kit contains: (a) a suitable polymerizable matrix material for filling the access chamber; (b) a syringe or other means for extruding the filler material into the root canal access cavity following placement of the conical device(s) and (c) a set of conical devices. With the exception of endodontic files, the kit contains all the specialized material and equipment needed to form the dedicated access channels after the access chamber has been excavated using standard dental instruments. A particularly preferred polymerizable matrix material is glass ionomer having a radiopacity similar to the surrounding tooth when cured. In dentistry, glass ionomer is made by mixing a powder with polyacrylic acid (standard glass ionomer liquid). For creating dedicated root canal access channels by the procedure described herein, a suitable glass ionomer is made by mixing equal parts of two powders such as GC Fuji I Luting Cement powder (described in U.S. Pat. No. 4,342,677) and GC Miracle Mix powder without alloy particles (available from GC Corporation, 3737 West 127th Street, Chicago, Ill. 60658, USA) with a resin such as polyacrylic acid. A suitable means for extruding the filler is a syringe such as the Centrix C-R which employs a fillable disposable cartridge such as the Centrix Accudose Needle Tubes (U.S. Pat. Nos. 5,052,927 and 5,122,057) both of which are available from Centrix, Inc. 770 River Road, Shelton, Conn. 064841, USA. The filler material is hand-mixed and the cartridge or "needle tube" is filled with the uncured filler and placed in the syringe for extrusion into the access chamber. An assortment of conical devices in accordance with the present invention completes the basic kit.

The kit may also include an additional item which is useful for positioning the conical devices prior to curing the surrounding polymerizable matrix material in the access chamber. The device, referred to herein as a file separator, is shown in FIG. 7. The file separator 71 comprises a thin (approximately 0.75 mm thick) planar sheet of plastic having an edge dimension of about 5 mm with a serrated or scalloped periphery 72. The file separator 71 may be used to orient and separate the shanks or handles of the files emerging from the root canals and respective conical devices while the projection matrix cures. The file separator 71 is placed between the files which are being employed to align the conical devices with the respective root canal orifices being accessed. The file separator 71 prevents the files (and the conical devices) from "wandering" during curing and establishes and maintains a spatial relationship between the various root canal access channels. While the size of the file separator should be on the order of about 5 mm, the general shape of the file separator 71 is not critical. The scalloped periphery 72 provides a plurality of detents for orienting and holding the file shanks.

Figure 8:
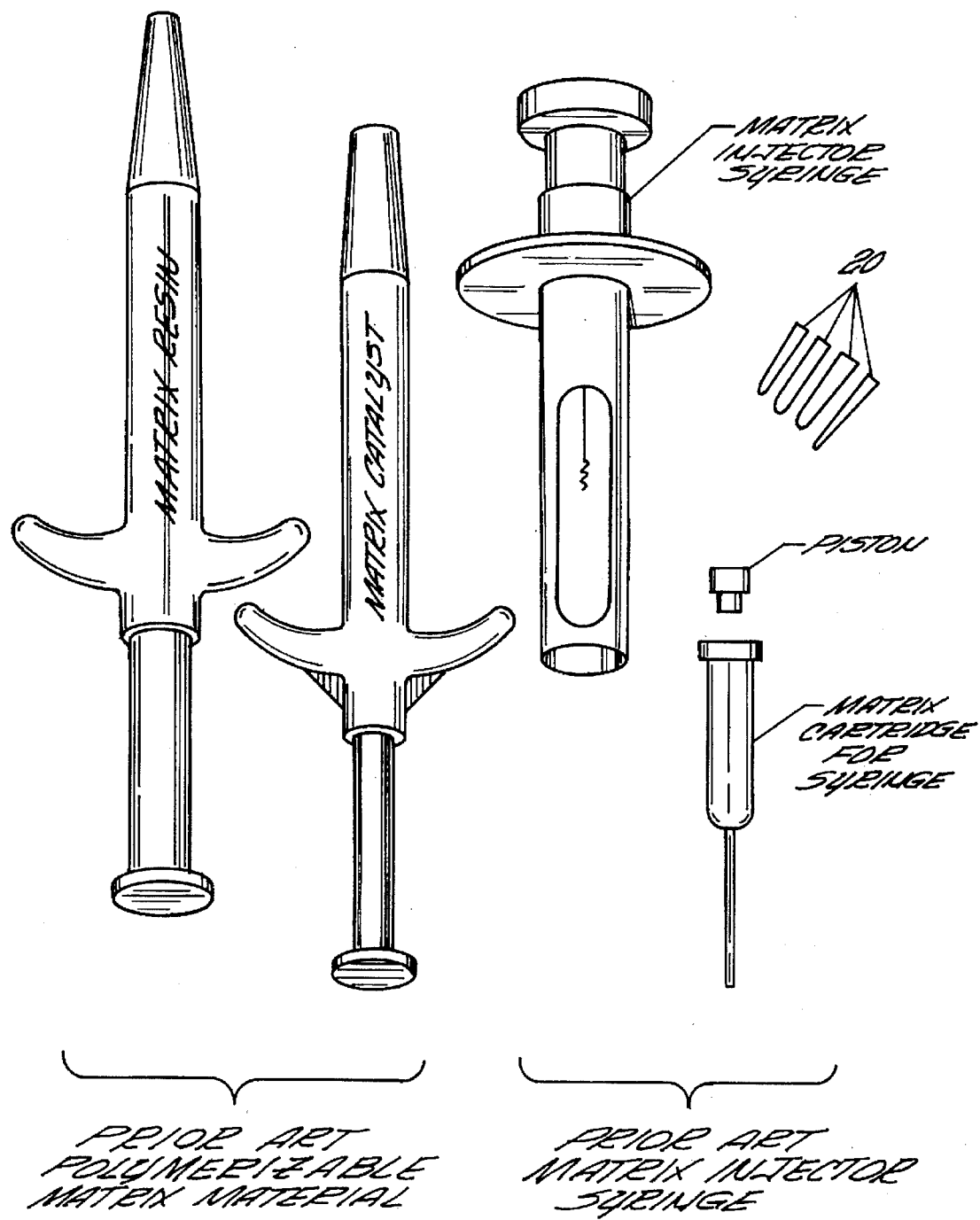
FIG. 8 is a top plan view of a kit in accordance with an embodiment of the present invention.
Figure 8A:
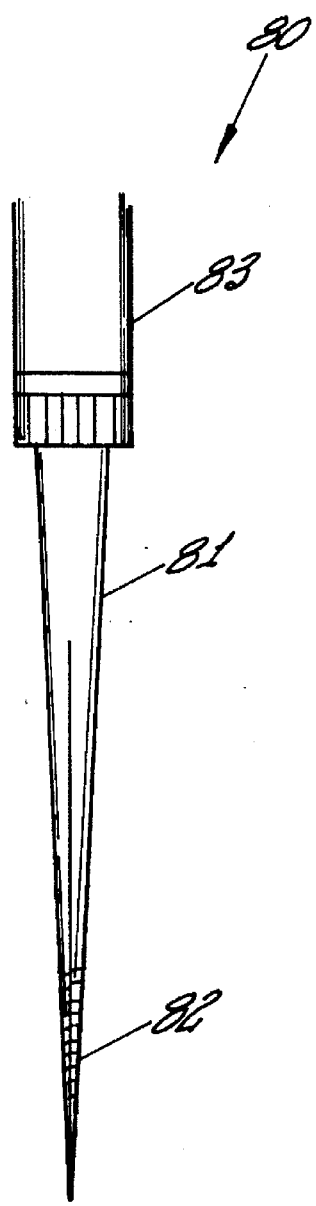
FIGS. 8(a) and 8(b) are side views of an alternative embodiment of the present invention wherein the conical member is either unitary with an endodontic file (FIG. 8(a)) or is permanently affixed to the shaft of a root canal file (FIG. 8(b)).
Figure 8B:
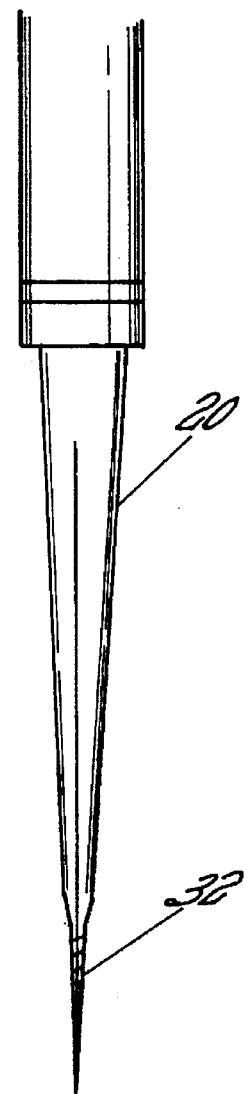

The conical device(s) of the present invention may also be either unitary with or permanently affixed to the shaft of a root canal file as shown in FIGS. 8(a) and 8(b). When employing the Unitary embodiment of the conical device shown in FIG. 8(a), the tip 82 of the file 80 is inserted into the root canal wherein the fluted portion of the tip 82 engages the walls of the root canal. The glass ionomer may then be injected around the conical device 81. Following curing of the resin, the conical device 81 is removed by removing the file. This embodiment can be viewed as a conical device having a "handle" portion for placement and removal and a "fluted tip" for insertion into the root canal. As can be seen in FIGS. 8(a) and 8(b), the fluted tip potions 82 and 32 extend beyond the conical device portions 81 and 20 of the respective files. Accordingly, since the conical device 80 is unitary with the file, it does not have a hollow central lumen to accommodate the shaft of a (separate) root canal file. In the embodiment of the invention shown in FIG. 8(b), the conical device 20 of the present invention is shown non-removably affixed by, for example, an adhesive, to the shaft 32 of a root canal file. The embodiment of the device having the conical device integral (and unitary) with the file shaft as shown in FIG. 8(a) is preferably made from metal with the conical device portion 81 having a polished outer surface to facilitate release from the matrix material. The affixed embodiment; that is, the embodiment having a standard conical device 20 affixed to the shaft of a standard file as shown in FIG. 8(b) is preferably made by insertion molding a conical device 20 over an endodontic file to provide a device similar to that shown in FIG. 3(b) but in which the conical device is integral with, and not separable from, the file.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A device for creating a dedicated access channel extending from the surface of a tooth to a root canal orifice within said tooth wherein said root canal orifice has been exposed by creating an access chamber between said surface of said tooth and said root canal orifice and wherein said access chamber is at least partially filled with a polymerizable matrix material, said device comprising (a) an endodontic file having a handle and a shank; and
    (b) the frustum of a cone, said frustum having an axial central lumen and a wide end and a narrow end and an outer surface therebetween, said narrow end having an outer diameter approximately equal to the diameter of said root canal, and wherein axial central lumen is dimensioned to snugly accommodate said shank of said endodontic file adapted to be inserted therein, and wherein said outer surface releases said polymerizable matrix material when said matrix material is cured, thereby leaving the formed dedicated access channel accessible for reintroduction of said shank of said endodontic file.

2. A method for creating a dedicated access channel in a tooth, said dedicated access channel extending from a surface of said tooth to a root canal orifice within said tooth, said method comprising the steps of:

(a) exposing said root canal orifice by excavating an access chamber extending from said surface of said tooth to said root canal orifice;
    (b) advancing an endodontic file having a shank with a sharp tip through a central lumen of a cone-shaped device so that the sharp tip of said fie projects beyond said narrow end of said cone-shaped device;
    (c) introducing said sharp tip of said endodontic filed into said root canal orifice;
    (d) injecting a polymerizable matrix material into said access chamber to at least partially fill said access chamber;
    (e) sliding said cone-shaped device down said shank of said file until said narrow end of said cone-shaped device is in juxtaposition with said root canal orifice;
    (f) allowing said polymerizable matrix material to at least partially cure; and
    (g) removing said device from said at least partially cured matrix material thereby creating said dedicated access channel.

3. The method according the claim 2 wherein steps (d) and (e) are reversed.

4. A kit for creating a dedicated access channel in a tooth wherein the channel extends from a surface of the tooth to a root canal orifice within the tooth, said kit comprising:

(a) a polymerizable matrix material;
    (b) means for injecting said polymerizable matrix material into the access channel of the tooth;
    (c) at least one substantially cone-shaped member having a wide end and a narrow end and a central lumen therebetween, said narrow end having an outer diameter dimensioned to enter a root canal orifice.

5. The kit of claim 4 wherein said cone-shaped member has an outer surface which releases said polymerizable matrix material when said polymerizable matrix material is cured.

6. The kit according to claim 5 further comprising a file separator.

7. A device for creating a dedicated access channel extending from the surface of a tooth to a root canal orifice within said tooth wherein said root canal orifice has been exposed by creating an access chamber between said surface of said tooth and said root canal orifice and wherein said access chamber is at least partially filled with a polymerizable matrix material, said device comprising (a) an endodontic file having a handle and a shank; and (b) the frustum of a cone, said frustum having an axial central lumen and a wide end and a narrow end and an outer surface therebetween, said narrow end having an outer diameter approximately equal to the diameter of said root canal orifice, said wide end being coated with a contact adhesive, and wherein axial central lumen is dimensioned to snugly accommodate said shank of said endodontic file and wherein said outer surface releases said narrow end having an outer diameter approximately equal to the diameter of said root canal when said matrix material is cured.

* * * * *